United States Patent
Khandkar et al.

(10) Patent No.: US 6,846,327 B2
(45) Date of Patent: Jan. 25, 2005

(54) RADIOLUCENT BONE GRAFT

(75) Inventors: Ashok C. Khandkar, Salt Lake City, UT (US); Mahendra S. Rao, Timonium, MD (US)

(73) Assignee: Amedica Corporation, Salt Lake City, UT (US)

( * ) Notice: Subject to any disclaimer, the term of this patent is extended or adjusted under 35 U.S.C. 154(b) by 301 days.

(21) Appl. No.: 10/137,106

(22) Filed: Apr. 30, 2002

(65) Prior Publication Data

US 2003/0009225 A1 Jan. 9, 2003

Related U.S. Application Data (60) Provisional application No. 60/287,824, filed on May 1, 2001.

(51) Int. Cl.[7] .................................................. A61F 2/28
(52) U.S. Cl. .................................................. 623/16.11
(58) Field of Search ............................ 623/11.11, 16.11

(56) References Cited

U.S. PATENT DOCUMENTS

| | | | | |
|---|---|---|---|---|
| 6,261,586 B1 | * | 7/2001 | McKay | 424/423 |
| 6,277,149 B1 | * | 8/2001 | Boyle et al. | 623/17.16 |
| 6,346,123 B1 | * | 2/2002 | McKay | 623/17.11 |
| 6,398,811 B1 | * | 6/2002 | McKay | 623/17.16 |
| 6,494,883 B1 | * | 12/2002 | Ferree | 606/61 |
| 2002/0111680 A1 | * | 8/2002 | Michelson | 623/17.11 |
| 2002/0143403 A1 | * | 10/2002 | Vaidyanathan et al. | 623/23.51 |
| 2003/0050709 A1 | * | 3/2003 | Noth et al. | 623/23.58 |

* cited by examiner

*Primary Examiner*—Kevin Shaver
*Assistant Examiner*—Michael B. Priddy
(74) *Attorney, Agent, or Firm*—Kelly Lowry & Kelley, LLP (57) ABSTRACT

An improved ceramic bone graft is provided for human implantation, particularly such as a spinal fusion cage for implantation into the inter-vertebral space between two adjacent vertebrae. The improved spinal fusion cage includes a substrate block of high strength ceramic having a selected size and shape to fit the anatomical space, and a controlled porosity analogous to natural bone. The substrate block is coated with a bio-active surface coating material such as hydroxyapatite or a calcium phosphate to promote bone ingrowth and enhanced bone fusion. Upon implantation, the fusion cage provides a spacer element having a desired combination of mechanical strength together with osteoconductivity and osteoinductivity to promote bone ingrowth and fusion, as well as radiolucency for facilitated post-operative monitoring. The fusion cage may additionally carry one or more natural or synthetic therapeutic agents for further promoting bone ingrowth and fusion.

45 Claims, 4 Drawing Sheets

RADIOLUCENT BONE GRAFT

This application claims the benefit of U.S. Provisional Application No. 60/287,824, filed May 1, 2001.

BACKGROUND OF THE INVENTION

This invention relates generally to improvements in bone grafts such as spinal fusion cages of the type designed for human implantation between adjacent spinal vertebrae, to maintain the vertebrae in substantially fixed spaced relation while promoting interbody bone ingrowth and fusion therebetween. More particularly, this invention relates to an implantable bone graft such as a spinal fusion cage having an improved combination of enhanced mechanical strength together with osteoinductive and osteoconductive properties, in a ceramic-based device that additionally and beneficially provides radiolucency for facilitated post-operative monitoring.

Implantable interbody bone grafts such as spinal fusion devices are known in the art and are routinely used by spine surgeons to keep adjacent vertebrae in a desired spaced-apart relation while interbody bone ingrowth and fusion takes place. Such spinal fusion devices are also used to provide weight bearing support between adjacent vertebral bodies and thus correct clinical problems. Such spinal fusion devices are indicated for medical treatment of degenerative disc disease, discogenic low back pain and spondylolisthesis. These conditions have been treated by using constructs, typically made from metals such as titanium or cobalt chrome alloys such as used in orthopedic implants, and allograft (donor) or autograft (patient) bone to promote bone ingrowth and fusion.

Typical interbody spinal fusion devices, such as plugs for example, have hollow or open spaces that are usually filled with bone graft material, either autogenous bone material provided by the patient or allogenous bone material provided by a third party donor. These devices also have lateral slots or openings which are primarily used to promote ingrowth of blood supply and grow active and live bone. These implants may also have a patterned exterior surface such as a ribbed or serrated surface or a screw thread to achieve enhanced mechanical interlock between adjacent vertebrae, with minimal risk of implant dislodgement from the site. See, for example, U.S. Pat. Nos. 5,785,710; and 5,702,453. Typical materials of construction for such interbody spinal fusion devices include bio-compatible carbon fiber reinforced polymers, cobalt chrome alloys, and stainless steels or titanium alloys. See, for example, U.S. Pat. No. 5,425,772.

Most state-of-the-art spinal fusion implants are made from titanium alloy and allograft (donor) bone, and have enjoyed clinical success as well as rapid and widespread use due to improved patient outcomes. However, titanium-based implant devices exhibit poor radiolucency characteristics, presenting difficulties in post-operative monitoring and evaluation of the fusion process due to the radio-shadow produced by the non-lucent metal. There is also clinical evidence of bone subsidence and collapse which is believed to be attributable to mechanical incompatibility between natural bone and the metal implant material. Moreover, titanium-based implant devices are primarily load bearing but are not osteoconductive, i.e., not conducive to direct and strong mechanical attachment to patient bone tissue, leading to potential graft necrosis, poor fusion and stability. By contrast, allograft bone implants exhibit good osteoconductive properties, but can subside over time as they assimilate into natural bone. Further, they suffer from poor pull out strength resulting in poor stability, primarily due to the limited options in machining the contact surfaces. Allograft bone implants also have variable materials properties and, perhaps most important of all, are in very limited supply. A small but finite risk of disease transmission with allograft bone is a factor as well. In response to these problems some developers are attempting to use porous tantalum-based metal constructs, but these have met with limited success owing to the poor elastic modulii of porous metals.

A typical titanium alloy spinal fusion device is constructed from a hollow cylindrical and externally threaded metal cage-like construct with fenestrations that allow communication of the cancellous host tissue with the hollow core, which is packed with morselized bone graft material. This design, constrained by the materials properties of titanium alloys, relies on bony ingrowth into the fenestrations induced by the bone graft material. However, the titanium-based structure can form a thin fibrous layer at the bone/metal interface, which degrades bone attachment to the metal. In addition, the hollow core into which the graft material is packed may have sub-optimal stress transmission and vascularization, thus eventually leading to failure to incorporate the graft. Mechanical stability, transmission of fluid stress, and the presence of osteoinductive agents are required to stimulate the ingrowth of vascular buds and proliferate mesenchymal cells from the cancellous host tissue into the graft material. However, most titanium-based spinal fusion devices in use today have end caps or lateral solid walls to prevent egress of the graft outwardly from the core and ingress of remnant disc tissue and fibroblasts into the core.

Autologous (patient) bone fusion has been used in the past and has a theoretically ideal mix of osteoconductive and osteoinductive properties. However, supply of autologous bone material is limited and significant complications are known to occur from bone harvesting. Moreover, the costs associated with harvesting autograft bone material are high, requiring two separate incisions, with the patient having to undergo more pain and recuperation due to the harvesting and implantation processes. Additionally, autologous cancellous bone material has inadequate mechanical strength to support intervertebral forces by itself, whereby the bone material is normally incorporated with a metal-based construct.

Ceramic materials provide potential alternative structures for use in spinal fusion implant devices. In this regard, monolithic ceramic constructs have been proposed, formed from conventional materials such as hydroxyapatitie (HAP) and/ortricalcium phosphate (TCP). See, for example, U.S. Pat. No. 6,037,519. However, while these ceramic materials may provide satisfactory osteoconductive and osteoinductive properties, they have not provided the mechanical strength necessary for the implant.

Thus, a significant need exists for further improvements in and to the design of bone grafts such as spinal fusion implant devices, particularly to provide a high strength implant having high bone ingrowth and fusion characteristics, together with substantial radiolucency for effective and facilitated post-operative monitoring.

Hence, it is an object of the present invention to provide an improved bone graft such as an interbody spinal fusion implant or cage made from a bio-compatible open pore structure, which has a radiolucency similar to that of the surrounding bone. It is also an object of the present invention to provide a substrate of high bio-mechanical strength for carrying biological agents which promote intervertebral bone ingrowth, healing and fusion. It is a further objective of the present invention to provide an interbody fusion device which has mechanical properties that substantially match that of natural bone, by using ceramic construct materials rather than metal.

SUMMARY OF THE INVENTION

In accordance with the invention, an improved bone graft such as a spinal fusion cage is provided for human implantation into the space between a pair of adjacent vertebrae, following removal of disc material between endplates of the adjacent vertebrae, to maintain the adjacent vertebrae in a predetermined and substantially fixed spaced relation while promoting interbody bone ingrowth and fusion. In this regard, the improved spinal fusion cage of the present invention is designed for use in addressing clinical problems indicated by medical treatment of degenerative disc disease, discogenic lower back pain, and spondylolisthesis.

The improved bone graft, as embodied in the form of the improved spinal fusion cage, comprises a porous or open-celled substrate block formed from a ceramic composition having a relatively high bio-mechanical strength and load bearing capacity. A preferred composition for the ceramic substrate block comprises a two phase alumina-zirconia composition having a suitable size and shape for seated implantation into the inter-vertebral space, with generally planar or appropriately shaped faces seated respectively upon the endplates of the adjacent vertebrae. In a preferred form, the substrate block comprises an alumina-zirconia composition with an alumina to zirconia ratio ranging from about 100% (i.e., 2:1) to about 25% (i.e., 1:4). More preferably, the substrate block composition comprises about 10% to about 20% by volume zirconia in alumina. Either yttria stabilized zirconia (about 2.5 to about 5 mol % yttria in zirconia) or ceria stabilized zirconia (about 2.5 to about 15 mol % ceria in zirconia) is preferably used for the zirconia phase. The substrate block is porous, having a porosity of about 10% to about 50% by volume with open pores distributed throughout and a pore size range of from about 5 to about 500 microns. In a preferred form, the porosity of the substrate block is gradated from a first relatively low porosity region emulating or mimicking the porosity of cortical bone to a second relatively higher porosity region emulating or mimicking the porosity of cancellous bone.

The porous substrate block is internally and externally coated with a bio-active surface coating material selected for relatively high osteoconductive and osteoinductive properties, such as a hydroxyapatite or a calcium phosphate material.

The thus-formed bone graft can be made in a variety of shapes and sizes to suit different specific implantation requirements. Preferred shapes include cylindrical or partly cylindrical with substantially flat opposite ends and a tapered or lordotic cross section to suit the required curvature of the inter-vertebral space, in the case of a spinal fusion device. The exterior surface of the cylindrical body may include threads or ribs for facilitated and secure screw-in placement, for example, between adjacent vertebrae. Alternative preferred shapes include a generally rectangular block which may also include serrations or the like on one or more exterior faces thereof, and/or may have a tapered or lordotic cross section for improved fit into the inter-vertebral space. The bone graft may desirably include a posterior end having an engagement means such as a threaded socket for releasible engagement with a suitable insertion tool. In addition, the bone graft may also include one or more laterally open recesses or bores for receiving and supporting osteoconductive bone graft material, such as allograft (donor) or autograft (patient) material.

Further alternative bone graft configurations may include controlled porosity gradations to define a relatively low porosity first region or regions substantially emulating cortical bone, to define a high strength loading bearing zone or strut for absorbing impaction and insertion load, in combination with one or more relatively high porosity second regions substantially emulating cancellous bone for contacting adjacent patient bone for enhanced bone ingrowth and fusion.

The resultant bone graft exhibits relatively high mechanical strength for load bearing support, for example, between adjacent vertebrae in the case of a spinal fusion cage, while additionally and desirably providing high osteoconductive and osteoinductive properties to achieve enhanced bone ingrowth and interbody fusion. Importantly, these desirable characteristics are achieved in a structure which is substantially radiolucent so that the implant does not interfere with post-operative radiographic monitoring of the fusion process.

In accordance with a further aspect of the invention, the bone graft may additionally carry one or more therapeutic agents for achieving further enhanced bone fusion and ingrowth. Such therapeutic agents may include natural or synthetic therapeutic agents such as bone morphogenic proteins (BMPs), growth factors, bone marrow aspirate, stem cells, progenitor cells, antibiotics, or other osteoconductive, osteoinductive, osteogenic, or any other fusion enhancing material or beneficial therapeutic agent.

Other features and advantages of the invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
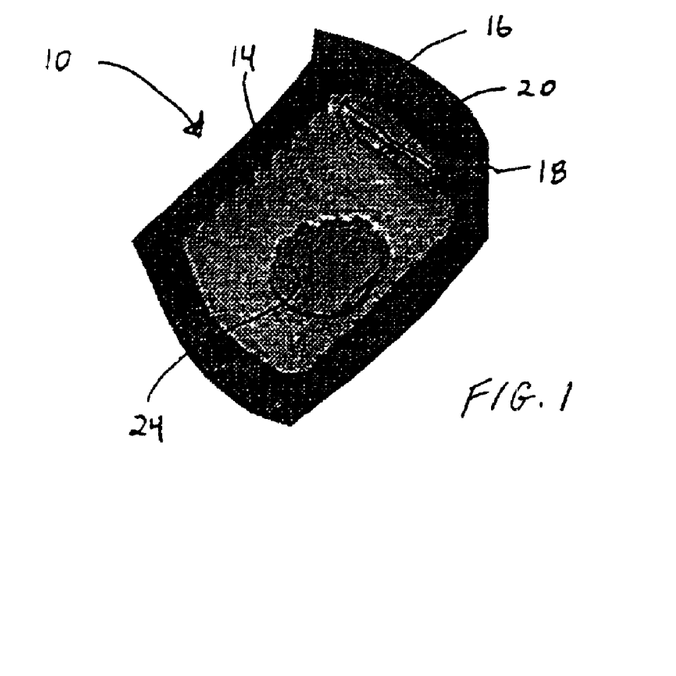
FIG. 1 is a perspective view illustrating an externally threaded radiolucent bone graft such as a spinal fusion cage having an externally threaded and generally cylindrical shape in accordance with one preferred for of the invention.
Figure 2:
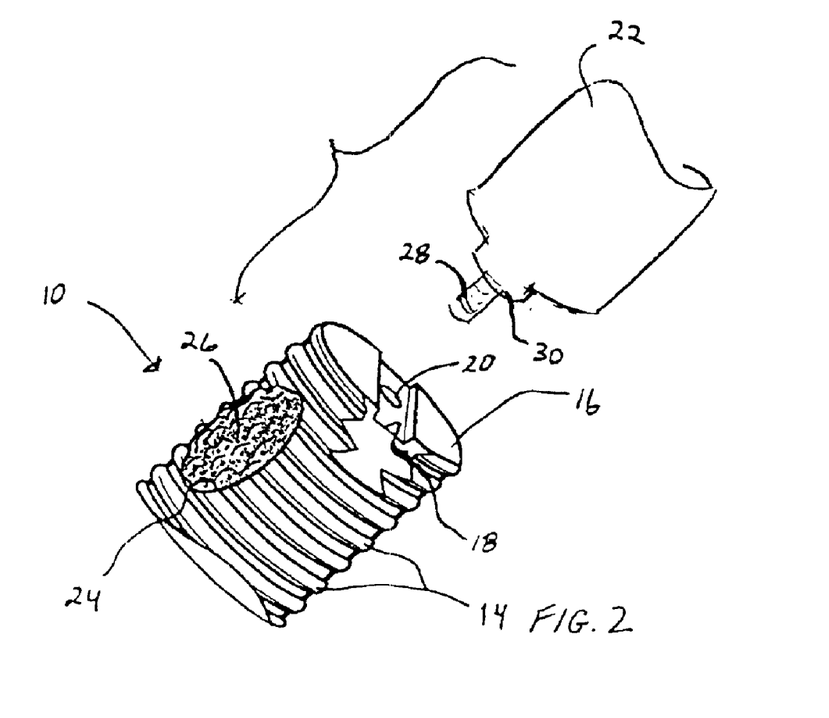
FIG. 2 is a perspective view showing the spinal fusion cage of FIG. 1 in exploded relation with a tip end of an associated insertion tool for use in implanting the spinal fusion cage into the inter-vertebral space between a pair of adjacent vertebrae in a patient.
Figure 3:
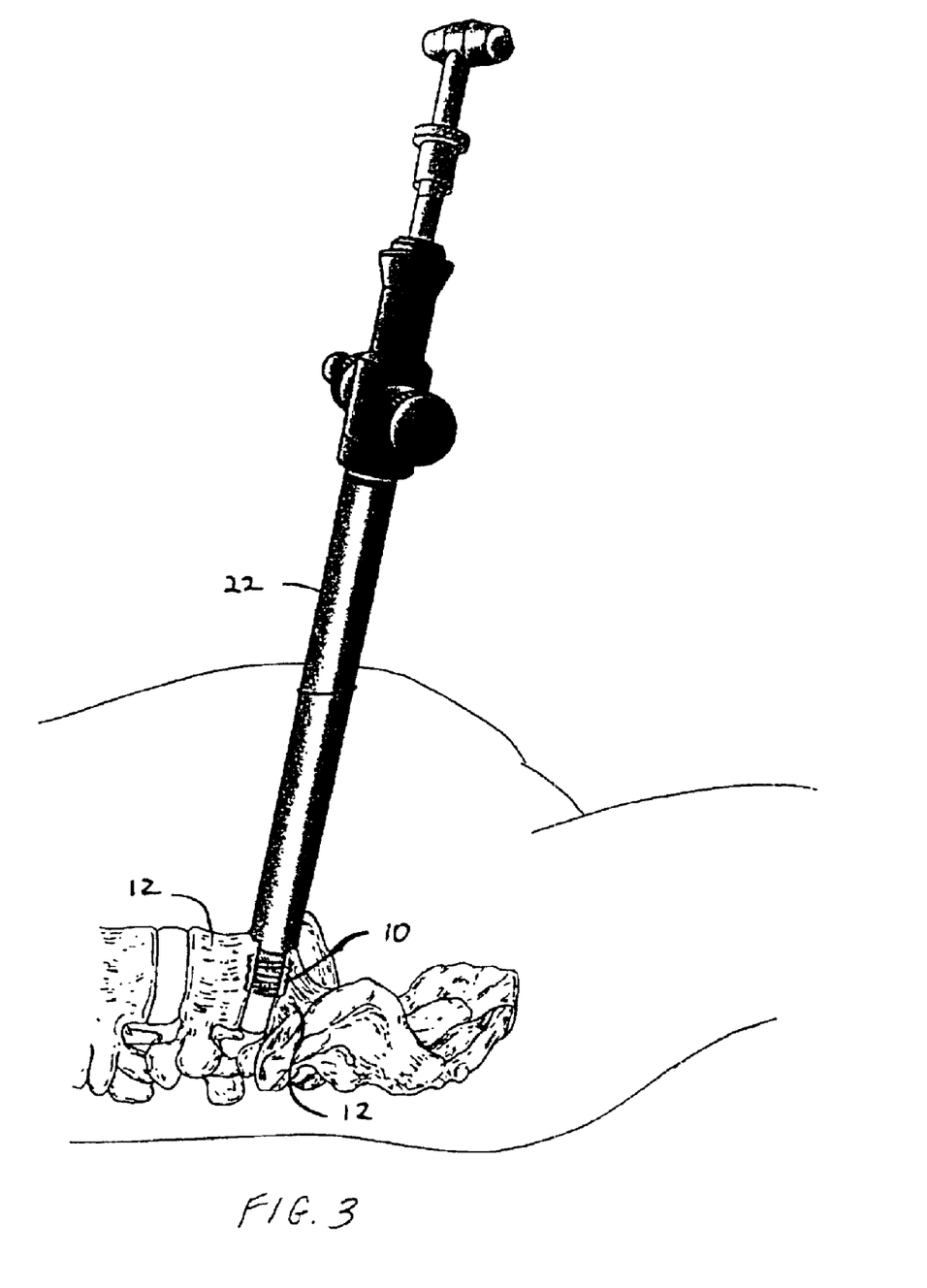
FIG. 3 is a perspective view showing implantation of the spinal fusion cage into the inter-vertebral space.

As shown in the exemplary drawings, a radiolucent bone graft such as a spinal fusion cage referred to generally in FIGS. 1–3 by the reference numeral 10 is provided for seated implantation between a pair of adjacent patient bones such as spinal vertebrae 12 (FIG. 3) to maintain the vertebrae in spaced relation while promoting interbody bone ingrowth and fusion. In general, the improved bone graft 10 comprises a bio-compatible ceramic substrate having a porous construction to define an open lattice conducive to interbody bone ingrowth and fusion, while providing a strong mechanical load bearing structure analogous to the load bearing properties of cortical and cancellous bone. This open-celled ceramic substrate is coated internally and externally with a bio-active surface coating selected for relatively strong osteoconductive and osteoinductive properties, whereby the coated ceramic substrate provides a scaffold conducive to cell attachment and proliferation to promote interbody bone ingrowth and fusion attachment. The ceramic substrate may also carry one or more selected therapeutic agents suitable for bone repair, augmentation and other orthopedic uses.

FIGS. 1–3 illustrate the improved bone graft in the form of an improved spinal fusion cage 10 in accordance with one preferred embodiment, in the shape of a generally cylindrical body having external ribs formed thereon in the shape of a screw thread 14. The opposite ends of this cylindrical body are generally flat, with a posterior end 16 shown to include a shallow diametrically extending notch 18 in combination with an axially centered and rearwardly open threaded socket 20 for releasable engagement with an insertion tool 22 (FIGS. 2–3), as will be described in more detail. The cylindrical body is shown further to include a laterally open recess or bore 24 for receiving and supporting morselized bone graft material 26 (FIG. 2), such as allograft bone material from a third party donor, or autograft bone material from the patient.

The preferred ceramic substrate composition comprises a relatively high strength ceramic substrate block. In accordance with one preferred form of the invention, this substrate block comprises a two phase alumina-zirconia composition having a controlled porosity and having a suitable size and shape for seated implantation, such as into the inter-vertebral space in the case of the spinal fusion cage 10. In a preferred form, the composition comprises an alumina-zirconia composition with an alumina to zirconia ratio ranging from about 100% (i.e., 2:1) to about 25% (i.e., 1:4). More preferably, the substrate composition comprises about 10% to about 20% by volume zirconia in alumina. Either yttria stabilized zirconia (about 2.5 to about 5 mol % yttria in zirconia) or ceria stabilized zirconia (about 2.5 to about 15 mol % ceria in zirconia) are preferably used for the zirconia phase.

The alumina-zirconia composition is processed to provide a homogeneous distribution of the two phases, and sintering temperatures are controlled to provide a particle size of about 0.5 micron or less in the sintered state. The resultant ceramic substrate block has a porosity ranging from about 2% to about 80% by volume, and preferably from about 10% to about 50% by volume, with pore sizes ranging from about 5 microns to about to about 1,500 microns, and preferably from about 100 to about 500 microns. In the preferred form, the pores are arranged for fluid continuity therebetween, and with a rough porous outer surface of large or extended surface area. Moreover, in the preferred form, the pores are arranged with a variable porosity gradient to define a first region of relatively low or reduced porosity (less than about 5%) mimicking cortical bone structure and a second region of relatively large or increased porosity (ranging from about 30% to about 80%) mimicking cancellous bone structure. In one preferred configuration, the outer or external surfaces of the reticulated substrate block comprise the first or low porosity region for improved load bearing capacity, while the interior surfaces of the substrate block comprises the second or high porosity region mimicking cancellous bone for enhance bone ingrowth and fusion. This material used to form the substrate block exhibits a substantially optimal combination of flexural strength (greater than about 500 MPa [mega-Pascals]) and fracture toughness (greater than about 5 Mpam$^{0.5}$ [mega-Pascal root meter]). These strengths are as measured for standard bend bars and single edge notched beam (SENB) specimens, per ASTM E-1304 and C-1162 procedures.

This high strength ceramic substrate block is surface-coated internally and externally with a bio-active organic or inorganic surface coating material selected for relatively strong osteoconductive and osteoinductive properties to provide a nutrient rich environment for cellular activity to promote interbody bone ingrowth and fusion attachment. Preferred surface coating materials comprise a resorbable material such as hydroxyapatite or a calcium phosphate ceramic. Alternative glassy (amorphous) materials having a relatively rich calcium and phosphate composition may also be used, particularly wherein such materials incorporate calcium and phosphate in a ratio similar to natural bone or hydroxyapatite. Such glassy compositions may comprise a partially or fully amorphous osteoinductive material comprising a composite of a glass and osteoinductive calcium compound, with a composition varying from about 100% glass to 100% osteoinductive calcium compound. The surface coating may also comprise autologous bone marrow aspirates.

The resultant bone graft 10 thus comprises the substrate block formed from the high strength ceramic material having bio-mimetic properties and which is nonresorbable, or slowly or infinitely slowly resorbable when implanted into the patient, in combination with the bio-active surface coating which is comparatively rapidly resorbable to promote rapid and vigorous bone ingrowth activity.

The substrate block may also advantageously be coated or impregnated with one or more selected therapeutic agents, for example, such as autologous, synthetic or stem cell derived growth factors or proteins and growth factors such as bone morphogenic protein (BMP) or a precursor thereto, which further promotes healing, fusion and growth. Alternative therapeutic agents may also include an antibiotic, or natural therapeutic agents such as bone marrow aspirates, and growth factors or progenitor cells such as mesenchymal stem cells, hematopoietic cells, or embryonic stem cells, either alone or as a combination of different beneficial agents.

More particularly, such therapeutic agent or agents can be applied to the bone graft 10 substantially at the time of or in the course of an implant surgical procedure, as by soaking the bone graft in the therapeutic agent or a liquid-based solution containing the therapeutic agent and then implanting the bone graft into the patient. In an alternative procedure, progenitor cells or the like can be taken from a specific patient and then cultured in vitro using the bone graft as a culture medium and substrate to produce a high and therapeutically effective concentration of the selected cells carried on and within the bone graft. Thereafter, the bone graft carrying the cultured cells can be surgically implanted. In one convenient configuration, the bone graft implant can be formed in the size and shape of a small pellet for suitable packing of multiple implants into a bone regeneration/ingrowth site.

The resultant bone graft such as the illustrative spinal fusion cage 10 exhibits relatively high bio-mechanical strength similar to the load bearing characteristics of natural bone. In addition, the spinal fusion cage 10 exhibits relatively strong osteoconductive and osteoinductive characteristics attributable primarily to the surface coating, again similar to natural bone. Importantly, the fusion cage 10 is also substantially radiolucent, so that the fusion cage does not interfere with post-operative radiological analysis of interbody bone ingrowth and fusion.

FIG. 2 illustrates the spinal fusion cage 10 with the bone graft material 26 carried within the laterally open bore 24, to achieve further enhanced bone ingrowth and fusion when the device is implanted into the intervertebral space. The insertion tool 22 includes a threaded tip 28 at a forward or nose end thereof for threaded engagement into the threaded socket 20 at the posterior end of the fusion cage 10. A locking abutment 30 is also provided at the forward end of the insertion tool 22 for seated engagement into the shallow notch 18 on the fusion cage. Thus assembled, the insertion tool 22 is used by a surgeon as viewed in FIG. 3 to seat the spinal fusion cage 10 into the space between a selected adjacent pair of vertebrae 12, with the fusion cage bearing against a substantial portion of the end plates of the two vertebrae on opposite sides of the inter-vertebral space. This insertion process may be accompanied by appropriate rotation of the insertion tool 22 so that the abutment 30 thereon rotatably drives the fusion cage 10 to the desired and securely seated implanted position. Then, the abutment 30 can be retracted from the fusion cage 10 followed by back-rotation of the threaded tip 28 for release from the fusion cage.

Figure 4:
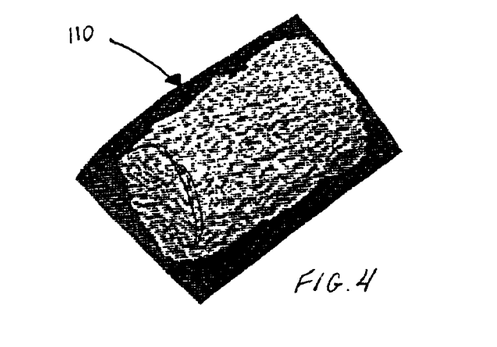
FIG. 4 is a perspective view depicting one alternative preferred and generally cylindrical bone graft such as a spinal fusion cage.
Figure 5:
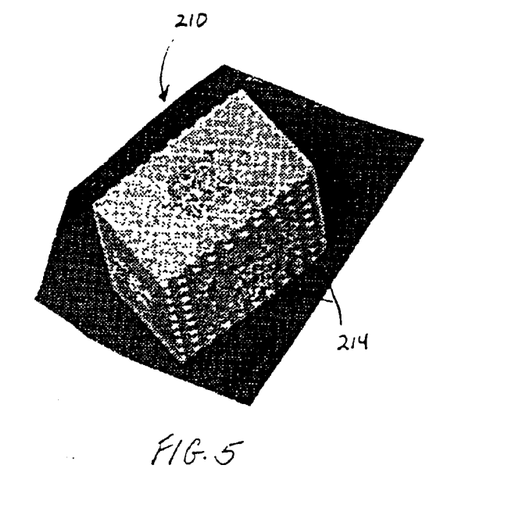
FIG. 5 is a perspective view depicting a further alternative preferred form of the invention, comprising a generally rectangular bone graft such as a spinal fusion cage having at least one serrated external surface.
Figure 6:
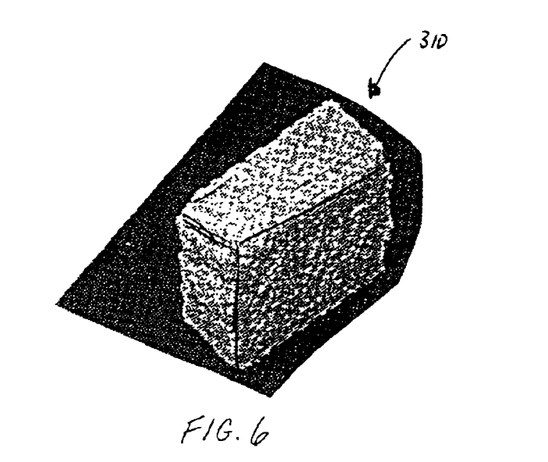
FIG. 6 is a perspective view showing still another alternative preferred form of the invention, comprising a generally rectangular bone graft such as a spinal fusion cage.

FIGS. 4-6 illustrate alternative configurations for improved bone grafts such as spinal fusion cages constructed in accordance with the present invention, it being recognized and understood that the bone graft can be constructed in a wide range of different geometric sizes and shapes. FIG. 4 shows a spinal fusion cage 110 having a generally cylindrical shape similar to the fusion cage 10 shown and described in FIGS. 1-3, but wherein the external screw thread 14 is omitted. As shown, the spinal fusion cage 110 (FIG. 4) has an open-celled structure defined by a high strength porous ceramic substrate block (as previously described) coated with the bio-active surface coating material, but wherein the cylindrical exterior surface is defined by the relatively rough open-lattice substrate structure having sufficient surface discontinuity and high surface area for optimized contact with cancellous bone to achieve substantially optimized bone ingrowth. FIG. 5 shows another alternative spinal fusion cage 210 comprising a surface-coated high strength porous ceramic substrate block (formed as previously described) with a generally rectangular block configuration to include at least one exterior surface to include a plurality of serrations 214 for securely mechanical locking with adjacent patient bones such as adjacent vertebrae 12 at opposite sides of the inter-vertebral space. FIG. 6 depicts an alternative rectangular block-shaped spinal fusion cage 310 comprising another surface-coated high strength porous ceramic substrate block (formed as previously described) having a narrower cross sectional dimension and an exterior surface defined by the relatively rough-textured open-lattice substrate (similar to FIG. 4). Each of the embodiments depicted in FIGS. 1-3 and FIGS. 4-6 has a height dimension and may be tapered or lordotic in shape (as shown in FIG. 6) for enhanced anatomical fit, for example, into the intervertebral space or the like.

Figure 7:
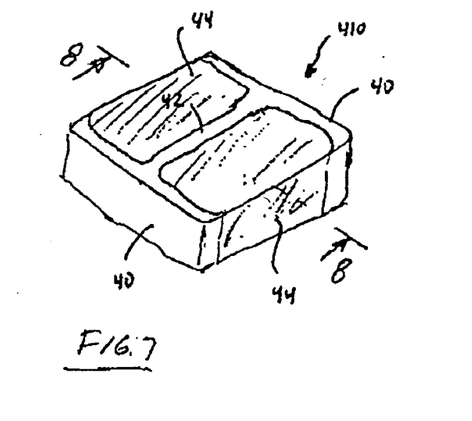
FIG. 7 is a perspective view showing a further alternative preferred form of the invention, comprising a generally rectangular bone graft such as a spinal fusion cage with localized regions of varying porosity.
Figure 8:
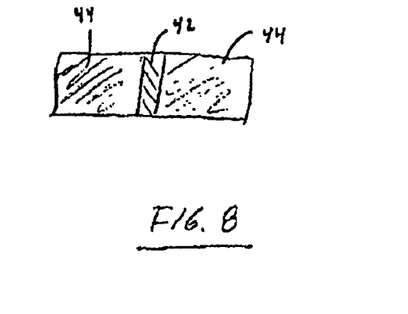
FIG. 8 is a transverse sectional view taken generally on the line 8—8 of FIG. 7.

FIGS. 7-10 depict further alternative preferred forms of the invention, wherein the porosity gradient within the high strength porous ceramic substrate block is controllably varied to provide desirable load bearing benefits consistent with bone ingrowth and fusion. More particularly, FIGS. 7-8 show a generally rectangular bone graft such as a spinal fusion cage 410 having a tapered height dimension in the anterior-posterior direction. The substrate block is formed with the first region 40 of relatively low porosity substantially mimicking cortical bone to extend across the anterior and posterior faces and further to include at least one interconnecting load bearing strut 42 shown in the illustrative drawings to extend centrally in an anterior-posterior direction within the body of the substrate block. The remainder of the substrate block comprises the second portion 44 of relatively high porosity substantially mimicking cancellous bone. The harder first region 40 including the central strut 42 beneficially provides a hard and strong load bearing structure capable of withstanding impaction and insertion forces in the anterior-posterior direction without damage to the implant, while the softer second region 44 presents an exposed and large surface area for substantially optimized interknitting ingrowth and fusion with adjacent patient bone. In a spinal fusion cage application, the medial-lateral faces of the implant are advantageously defined by the softer second region 44, wherein these regions are thus exposed to traditional medial-lateral X-ray imaging for post-operative radiological analysis of the implant/bone interface. Persons skilled in the art will recognize and appreciate that alternative configurations for the load bearing strut or struts 42 may be used, such as an X-shaped strut configuration extending in a cranial-caudial direction, in combination with or in lieu of the exterior faces 40 and/or the anterior-posterior central strut as shown.

Figure 9:
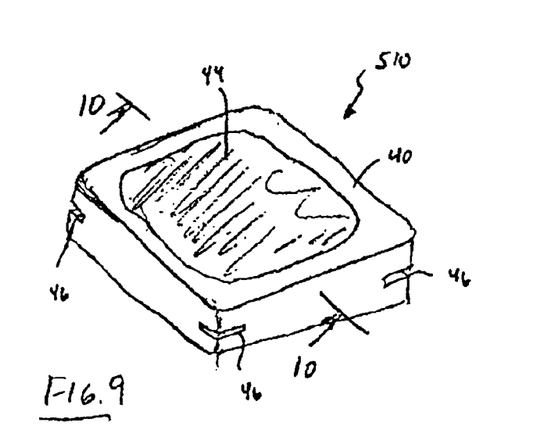
FIG. 9 is another perspective view showing a modified preferred form of the invention, comprising a generally rectangular bone graft such as a spinal fusion cage with alternative localized regions of varying porosity.
Figure 10:
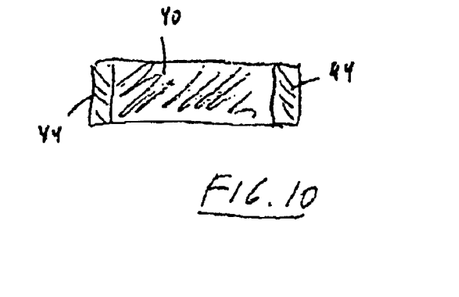
FIG. 10 is a transverse sectional view taken generally on the line 10—10 of FIG. 9.

FIGS. 9-10 show another generally rectangular bone graft such as a spinal fusion cage 510 having the tapered height dimension in the anterior-posterior direction. The substrate block is formed with the first region 40 of relatively low porosity substantially mimicking cortical bone to extend circumferentially about the substrate block in surrounding relation to the second portion 44 of relatively high porosity substantially mimicking cancellous bone. The harder first region 40 once again beneficially provides a hard and strong load bearing structure capable of withstanding impaction and insertion forces in the anterior-posterior direction without damage to the implant, and additionally provided high strength vertical load carrying capacity. By contrast, the softer second region 44 is vertically exposed to present a large surface area for substantially optimized interknitting ingrowth and fusion with adjacent patient bone. The external corners of the substrate block may incorporate laterally open slots 46 (FIG. 9) for convenient engagement by and manipulation with a suitable surgical tool (not shown).

In both of the embodiments of FIGS. 7-10, the substrate block comprises a high strength porous ceramic as previously described, and is coated with the bio-active surface coating material, again as previously described, to enhance bone ingrowth and fusion. The substrate block may also include one or more therapeutic agents. Persons skilled in the art will recognize and appreciate that the relatively low and high porosity regions 40 and 44 shown in FIGS. 7–10 will be integrally joined by a suitable albeit relatively narrow gradient region wherein the porosity transitions therebetween.

The improved bone graft such as the illustrative spinal fusion cage of the present invention thus comprises an open-celled substrate block structure which is coated with a bio-active surface coating, and has the strength required for the weight bearing capacity required of a fusion device. The capability of being infused with the appropriate biologic coating agent imparts desirable osteoconductive and osteoinductive properties to the device for enhanced interbody bone ingrowth and fusion, without detracting from essential load bearing characteristics. The radiolucent characteristics of the improved device beneficially accommodate post-operative radiological examination to monitor the bone ingrowth and fusion progress, substantially without undesirable radio-shadowing attributable to the fusion cage. The external serrations or threads formed on the fusion cage may have a variable depth to enable the base of the device to contact the cortical bone for optimal weight bearing capacity. In addition to these benefits, the present invention is easy to manufacture in a cost competitive manner. The invention thus provides a substantial improvement in addressing clinical problems indicated for medical treatment of degenerative disc disease, discogenic low back pain and spondylolisthesis.

The bone graft of the present invention provides at least the following benefits over the prior art:

[a] a porous osteoconductive scaffold for enhanced fusion rates;

[b] a bio-mimetic load bearing superstructure providing appropriate stress transmission without fatigue failure;

[c] a pore structure and size suitable for ingrowth and vascularization,

[d] the ability to absorb and retain an osteoinductive agent such as autologous bone marrow aspirate or BMPs;

[e] bio-inert and bio-compatible with adjacent tissue and selected for ease of resorption;

[f] fabricatable and machinable into various shapes;

[g] sterilizable; and

[h] low manufacturing cost.

A variety of further modifications and improvements in and to the spinal fusion cage of the present invention will be apparent to those persons skilled in the art. Accordingly, no limitation on the invention is intended by way of the foregoing description and accompanying drawings, except as set forth in the appended claims.

What is claimed is:

1. A bone graft, comprising:
   a porous ceramic substrate block having a relatively high strength corresponding substantially with natural cortical and cancellous bone, said porous ceramic substrate block having a first region of relatively low porosity substantially mimicking natural cortical bone, and a second region of relatively high porosity substantially mimicking cancellous patient bone; and
   a bio-active and resorbable surface coating applied to said substrate block, said surface coating having osteoconductive and osteoinductive properties to promote interbody bone ingrowth and fusion attachment with adjacent patient bone.

2. The bone graft of claim 1 wherein said porous ceramic substrate block comprises a ceramic structure formed from alumina, zirconia, or composition thereof.

3. The bone graft of claim 2 wherein said porous ceramic substrate block comprises an alumina-zirconia composition having an alumina to zirconia ratio ranging from about 100% to about 25%.

4. The bone graft of claim 2 wherein said porous ceramic substrate block comprises an alumina-zirconia composition having from about 10% to about 25% zirconia in alumina.

5. The bone graft of claim 1 wherein said porous ceramic substrate block is formed from a material with a flexural strength greater than about 500 mega-Pascals, and a fracture toughness greater than about 5 mega-Pascal root meter.

6. The bone graft of claim 1 wherein said porous ceramic substrate block has a porosity ranging from about 2% to about 80% by volume, and further wherein the pore size ranges from about 5 microns to about 1,500 microns.

7. The bone graft of claim 6 wherein said porosity ranges from about 10% to about 50% by volume, and wherein the pore sizes range from about 100 microns to about 500 microns.

8. The bone graft of claim 1 wherein said first region has a porosity of less than about 5%, and wherein said second region has a porosity ranging from about 30% to about 80%.

9. The bone graft of claim 1 wherein said substrate block further includes means for facilitated grasping and manipulation with a surgical instrument for implantation.

10. The bone graft of claim 1 wherein said bio-active surface coating is selected from the group consisting of hydroxyapatite and calcium compounds.

11. The bone graft of claim 1 wherein said bio-active surface coating comprises an organic coating material.

12. The bone graft of claim 11 wherein said organic coating material is selected from the group consisting of autologous bone marrow aspirates, bone morphogenic proteins, growth factors and progenitor cells, and mixtures thereof.

13. The bone graft of claim 12 wherein said progenitor cells include mesenchymal stem cells, hematopoietic cells, and embryonic stem cells.

14. The bone graft of claim 1 wherein said porous ceramic substrate block is substantially radiolucent.

15. The bone graft of claim 1 further including a therapeutic agent carried by said substrate block.

16. The bone graft of claim 15 wherein said therapeutic agent comprises a natural or synthetic osteoconductive or osteoinductive agent.

17. The bone graft of claim 1 wherein said substrate block has a rough exterior surface.

18. The bone graft of claim 1 wherein said substrate block has a ribbed exterior surface.

19. The bone graft of claim 1 wherein said substrate block has a laterally open bore formed therein, and further including an osteoconductive material supported within said bore.

20. The bone graft of claim 19 wherein said osteoconductive material comprises morselized bone graft material.

21. A bone graft, comprising:
   a porous ceramic substrate block having a relatively high strength corresponding substantially with natural cortical and cancellous bone, said porous ceramic substrate block having a variable porosity gradient substantially mimicking natural cortical and cancellous bone; and
   a bio-active and resorbable surface coating applied to said substrate block, said surface coating having osteoconductive and osteoinductive properties to promote interbody bone ingrowth and fusion attachment with adjacent patient bone.

22. A bone graft, comprising:
a porous ceramic substrate block having a relatively high strength corresponding substantially with natural cortical and cancellous bone; and
a bio-active and resorbable surface coating applied to said substrate block, said surface coating having osteoconductive and osteoinductive properties to promote interbody bone ingrowth and fusion attachment with adjacent patient bone;
said bio-active surface coating being internally and externally applied to said porous ceramic substrate block.

23. A bone graft, comprising:
a porous ceramic substrate block having a relatively high strength corresponding substantially with natural cortical and cancellous bone; and
a bio-active and resorbable surface coating applied to said substrate block, said surface coating having osteoconductive and osteoinductive properties to promote interbody bone ingrowth and fusion attachment with adjacent patient bone;
said bio-active surface coating comprising a partially or fully amorphous osteoinductive material including a glass and osteoinductive calcium compound.

24. A bone graft, comprising:
a porous ceramic substrate block having a relatively high strength corresponding substantially with natural cortical and cancellous bone; and
a bio-active and resorbable surface coating applied to said substrate block, said surface coating having osteoconductive and osteoinductive properties to promote interbody bone ingrowth and fusion attachment with adjacent patient bone;
the pores formed within said substrate block being in substantially open fluid communication sufficient to transmit fluid pressure therebetween.

25. A bone graft for implantation between and fusion with adjacent bone, comprising:
a substrate block having a relatively high strength corresponding substantially with natural cortical and cancellous bone, said substrate block having a first region of relatively low porosity substantially mimicking natural cortical bone, and a second region of relatively high porosity substantially mimicking cancellous patient bone; and
a bio-active and relatively rapidly resorbable surface coating applied to said substrate block, said surface coating having osteoconductive and osteoinductive properties to promote interbody bone ingrowth and fusion attachment with the adjacent bone;
said substrate block being relatively nonresorbable or resorbable at a rate substantially less than said surface coating.

26. A bone graft method, comprising the steps of:
forming a porous ceramic substrate block having a relatively high strength corresponding substantially with natural cortical and cancellous bone;
applying a bio-active and resorbable surface coating to said substrate block to form a bone graft implant, said surface coating having osteoconductive and osteoinductive properties to promote interbody bone ingrowth and fusion attachment with adjacent patient bone; and
surgically implanting the bone graft implant within a patient at a selected bone regeneration/ingrowth site.

27. The bone graft method of claim 26 wherein the porous ceramic substrate block comprises a ceramic structure formed from alumina, zirconia, or composition thereof.

28. The bone graft method of claim 26 wherein said substrate block forming step comprises forming the substrate block with a porosity ranging from about 2% to about 80% by volume, and further with a pore size ranging from about 5 microns to about 1,500 microns.

29. The bone graft method of claim 28 wherein said porosity ranges from about 10% to about 50% by volume, and wherein the pore sizes range from about 100 microns to about 500 microns.

30. The bone graft method of claim 26 wherein said substrate block forming step comprises forming the substrate block with a variable porosity gradient substantially mimicking natural cortical and cancellous bone.

31. The bone graft method of claim 26 wherein said substrate block forming step comprises forming the substrate block with a first region of relatively low porosity substantially mimicking natural cortical bone, and a second region of relatively high porosity substantially mimicking cancellous patient bone.

32. The bone graft method of claim 26 wherein said step of applying the bio-active surface coating comprises applying the bio-active surface coating internally and eternally to the substrate block.

33. The bone graft method of claim 26 wherein the bio-active surface coating is selected from the group consisting of hydroxyapatite and calcium compounds.

34. The bone graft method of claim 26 wherein the bio-active surface coating comprises a partially or fully amorphous osteoinductive material including a glass and osteoinductive calcium compound.

35. The bone graft method of claim 26 wherein the bio-active surface coating comprises an organic coating material.

36. The bone graft method of claim 35 wherein the organic coating material is selected from the group consisting of autologous bone marrow aspirates, bone morphogenic proteins, growth factors and progenitor cells, and mixtures thereof.

37. The bone graft method of claim 36 wherein said progenitor cells include mesenchymal stem cells, hematopoietic cells, and embryonic stem cells.

38. The bone graft method of claim 26 wherein the porous ceramic substrate block is substantially radiolucent.

39. The bone graft method of claim 26 further including the step of adding a therapeutic agent to the substrate block.

40. The bone graft method of claim 39 wherein said step of adding the therapeutic agent is subsequent to said step of applying the bio-active surface coating.

41. The bone graft method of claim 39 wherein the therapeutic agent comprises a natural or synthetic osteoconductive or osteoinductive agent.

42. The bone graft method of claim 39 wherein the therapeutic agent is selected from the group consisting of autologous bone marrow aspirates, bone morphogenic proteins, growth factors and progenitor cells, and mixtures thereof.

43. The bone graft method of claim 42 further including the steps of extracting the therapeutic agent from a patient, and culturing the therapeutic agent in vitro using the bone graft implant as a culture medium and substrate prior to said implanting step.

44. A bone graft method, comprising the steps of:
forming a porous ceramic bone graft implant;
extracting from a patient a therapeutic agent selected from the group consisting of autologous bone marrow aspirates, bone morphogenic proteins, growth factors and progenitor cells, and mixtures thereof;

culturing the therapeutic agent in vitro using the bone graft implant as a culture medium and substrate prior to implanting; and surgically implanting the bone graft implant within a patient at a selected bone regeneration/ingrowth site.

45. The bone graft method of claim 44 wherein the progenitor cells are mesenchymal stem cells, hematopoietic stem cells, embryonic stem cells, or a combination thereof.

* * * * *